US010082512B2

(12) United States Patent
Block et al.

(10) Patent No.: US 10,082,512 B2
(45) Date of Patent: *Sep. 25, 2018

(54) DIAGNOSIS OF LIVER PATHOLOGY THROUGH ASSESSMENT OF PROTEIN GLYCOSYLATION (75) Inventors: Timothy M. Block, Doylestown, PA (US); Anand Mehta, Lansdale, PA (US); Mary Ann Comunale, Bangor, PA (US)

(73) Assignee: Drexel University, Philadelphia, PA (US)

( * ) Notice: Subject to any disclaimer, the term of this patent is extended or adjusted under 35 U.S.C. 154(b) by 191 days.

This patent is subject to a terminal disclaimer.

(21) Appl. No.: 11/913,348

(22) PCT Filed: May 5, 2006

(86) PCT No.: PCT/US2006/017478
§ 371 (c)(1),
(2), (4) Date: May 1, 2008

(87) PCT Pub. No.: WO2006/121892
PCT Pub. Date: Nov. 16, 2006

(65) Prior Publication Data
US 2009/0208926 A1 Aug. 20, 2009

Related U.S. Application Data (60) Provisional application No. 60/677,941, filed on May 5, 2005.

(51) Int. Cl.
*G01N 33/68* (2006.01)
*G01N 33/574* (2006.01)
*G01N 33/576* (2006.01)

(52) U.S. Cl.
CPC ... *G01N 33/6893* (2013.01); *G01N 33/57438* (2013.01); *G01N 2333/4728* (2013.01); *G01N 2800/08* (2013.01); *G01N 2800/085* (2013.01); *G01N 2800/7028* (2013.01)

(58) Field of Classification Search
CPC ........... G01N 33/6842; G01N 33/5761; G01N 2333/42; G01N 2400/10; G01N 2800/085; G01N 35/0098; G01N 2400/00; G01N 33/5005; G01N 33/5008; G01N 33/5091; G01N 33/5333; G01N 3/6842; G01N 2333/4728; G01N 2800/08; G01N 33/6893; G01N 33/6851; G01N 33/6857; G01N 2333/924; G01N 2400/02; G01N 33/50; G01N 33/53; G01N 33/57469; C12N 9/1048; Y10S 436/827; Y10S 997/927; Y10S 435/975; C07K 2317/41; C07K 14/42; C07K 2317/52; C07K 2317/92; C07K 16/303; C07K 16/00; B01J 2219/00659; B01L 3/5085; C07H 3/06; A61K 2039/505; A61K 31/4045; A61K 47/48753; A61K 49/0052; A61K 45/06; A61K 31/715; A61K 39/39; A61K 39/3955; A61K 47/4823; A61K 47/48292; A61K 51/1093; A61K 52/1027; C12P 21/005; C12P 19/18; Y10T 436/43333

See application file for complete search history.

(56) References Cited

U.S. PATENT DOCUMENTS

| 4,786,592 | A | 11/1988 | Deal et al. |
| 5,338,689 | A * | 8/1994 | Yves et al. ..................... 436/518 |
| 5,605,807 | A | 2/1997 | Dennis |
| 6,830,895 | B2 * | 12/2004 | Andrews et al. ............ 435/7.32 |
| 7,273,711 | B1 * | 9/2007 | Marth ................ G01N 33/6842 435/4 |
| 7,335,512 | B2 | 2/2008 | Callewaert et al. |
| 7,776,550 | B2 * | 8/2010 | Block et al. ................... 435/7.1 |
| 8,183,000 | B2 * | 5/2012 | Block et al. ................... 435/7.1 |
| 2007/0037221 | A1 | 2/2007 | Block et al. |
| 2009/0166224 | A1 | 7/2009 | Yang et al. |
| 2009/0253180 | A1 * | 10/2009 | Block et al. .................... 435/86 |

FOREIGN PATENT DOCUMENTS

| JP | 2002-502037 | 1/2002 |
| WO | WO 01/35105 A1 | 5/2001 |
| WO | WO 2004/066808 A2 | 8/2004 |
| WO | WO2006/078725 A1 | 7/2006 |
| WO | WO 2006/121892 | 11/2006 |

OTHER PUBLICATIONS

Schmitt et al. J. Gene, Virol. 2004, vol. 85, pp. 2045-2053.*
Ryden et al. Clin. Chem. 1999, vol. 45, No. 11, pp. 2010-2012.*
Wang et al. J. Hepatology 1996, vol. 25, pp. 166-171.*
Nedegger et al. Transplantation Proceeding 2004, vol. 35, pp. 1554-1557.*
Um et al. J. Immunol. 2004, vol. 173, pp. 1772-1778.*
Naitoh et al. J. Gastroe. and Hepato. 1999, vol. 14, pp. 436-445.*
Yamamot et al. Human Reproduction 2001, vol. 16, No. 11, pp. 2438-2444.*
Lee et al. Biochemical and Biophysical Research Communications, vol. 303, Issue 2, 4 Apr. 2003, pp. 427-432.*
Weinberg et al. The Journal of Histovchemisty and Cytochemistry, 1991, vol. 39, No. 8, pp. 1143-1148.*
Callewaer et al. Nature Medicine 2004, vol. 10, vol. 10, pp. 429-434.*
Aoki et al. Biochemica et Biophysica Acta 1997, pp. 207-213.*
Routier et al. Journal. Immunological Methods 1998, vol. 213, pp. 113-130.*

(Continued)

*Primary Examiner* — Bao Q Li
(74) *Attorney, Agent, or Firm* — Baker & Hostetler LLP (57) ABSTRACT

Methods for diagnosing pathology of the liver in a subject suspected of having such pathology are disclosed. The methods comprise quantifiably detecting glycosylation, and more specifically fucosylation, on proteins in biological fluids, and comparing the detected glycosylation with reference values for the glycosylation of such proteins in healthy or disease states.

10 Claims, 4 Drawing Sheets

(56) References Cited

OTHER PUBLICATIONS

The catalog of GALAB technologies GmbH published on 2004, pp. 1-8.*
Naitoh et al. Journal of Gastroenterology and Hepatology, 1999, vol. 14, pp. 436-445.*
Kinoshita et al. Cancer Research, Nov. 1991, vol. 51, pp. 5888-5892.*
Harada et al. Analytical Biochemistry, 1987, vol. 164, pp. 374-381.*
Antonia S F do Nascimento et al. Glycobiology published Jan. 30, 2015, pp. 1-10.*
Block et al. PNAS 2005, vol. 102, No. 3, pp. 779-784.*
Gornik et al. Clinical Biochemostry, 1999, vol. 32, Issue 8, pp. 605-608.*
Srikrishna et al. Journal of Biological Chemistry, 1997, vol. 272, pp. 25743-25752.*
Youings et al. Biochem. J. 1996, vol. 314, pp. 621-630.*
Srikrishna et al. The Journal of Biological Chemistry, Oct. 1997, vol. 272, pp. 25843-25732.*
Amano, K., et al., "Production of functional lectin in pichia pastoris directed by cloned cDNA from aleuria aurantia," Biosci. Biotechnol. Biochem., 2003, 67(10), 2277-2279.
Block, T., et al., "Molecular viral oncology of hepatocellular carcinoma," Oncogene, 2003, 22, 5093-5107.
Block, T.M., et al., "Use of targeted glycoproteomics to identify serum glycoproteins that correlate with liver cancer in woodchucks and humans," Proceedings of the National Academy of Sciences of USA, National Academy of Science, Washington, D.C., 2005, 102(3), 779-784.
Bouyain S., et al., "An endogenous *Drosophila* receptor for glycans bearing α1,3-linked core fucose residues," J. Biol. Chem., 2002, 277, 22566-22572.
Brechot, C., "Hepatitis B and C viruses and primary liver cancer," Baillieres Clin. Gastroenterol., 1996, 10(2), 335-373.
Buamah, P.K., et al. "Serum alpha fetoprotein heterogeneity as a means of differentiating between primary hepatocellular carcinoma and hepatic secondaries," Clin. Chim. Acta, 1984, 139, 313-316.
Comunale, M.A. et al., "Comparative proteomic analysis of de-N-glycosylated serum from hepatitis B carriers reveals polypeptides that correlate with disease status," 2004 Proteomics 4:826-38.
Comunale, M.A. et al., "Proteomic Analysis of Serum Associated Fucosylated Glycoproteins in the Development of Primary Hepatocellular Carcinoma," 2006 J Proteome Research. 6:308-315.
Drake, R.R. et al., "Lectin Capture Strategies Combined with Mass Spectrometry for the Discovery of Serum Glycoprotein Biomarkers," 2006 Mol Cell Proteomics 5:1957-1967.
Drickamer, K., "C-type lectin-like domains," Curr. Opin. Struct. Biol., 1999, 9, 585-590.
El-Serag, H.B., et al., "Trends in survival of patients with hepatocellular carcinoma between 1977 and 1996 in the United States," Hepatology, 2001, 62-65.
Galili, U. et al., "One Percent of Human Circulating B Lymphocytes are Capable of Producing the Natural Anti-Gal Antibody," 1993 Blood 82:2485-93.
Guile, G.R. et al., "A Rapid High-Resolution High-Performance Liquid Chromatographic Method for Separating Glycan Mixtures and analyzing Oligosaccharide Profiles," 1996. Anal Biochem 240:210-26.
Guile, G.R.et al., "Identification of highly fucosylated N-linked oligosaccharides from the human parotid gland," 1998. Eur J Biochem 258:623-56.
Harlow et al. (Eds.), Antibodies a Laboratory Manual; Cold Spring Harbor Laboratory; Cold Spring Harbor, NY, 1988, Chapter 6, 139-243.
Hoofnagle, J.H., et al. "The treatment of chronic viral hepatitis," N. Engl. J. Med., 1997, 336(5), 47-56.
Ikeda K, et al. "A multivariate analysis of risk factors for hepatocellular carcinogenesis: a prospective observation of 795 patients with viral and alcoholic cirrhosis," Hepatology 18, 1993, 47-53.
Ishak, K. et al., "Histological grading and staging of chronic hepatitis," J. Hepatol, 1995, 22, 696-699.
Ishida, H., et al. "Molecular cloning and overexpression of flea gene encoding a fucose-specific lectin of aspergillus oryzae," Biosci. Biotechnol. Biochem., 2002, 66(5), 1002-1008.
Kaneko, Y. et al., "Anti-Inflammatory Activity of Immunoglobulin G Resulting from Fc Sialylation," 2006 Science 313:670-3.
Kinoshita, N. et al., "α-Fetoprotein antibody-lectin enzyme immunoassay to characterize sugar chains for the study of liver diseases," Clinica Acta, 1989, 179, 143-152.
Köhler, G., et al., "Continuous cultures of fused cells secreting antibody of predefined specificity," Nature, 1975, 256, 495-497.
Kweon, Y-O. et al., "Decreasing fibrogenesis: an immunohistochemical study of paired liver biopsies following lamivudine therapy for chronic hepatitis B," 2001 B. J Hepatol 35:749-55.
Lastra,, G.C. et al., "Changes in the Galactose Content of IgG during Humoral Immune Responses," 1998. Autoimmunity 28:25-30.
Liljeblad M., et al., "A lectin immunosensor technique for determination of alphal-acid glycoprotine fucosylation," Analytical Biochemistry, 2001, 288(2), 216-224.
Loris, R., et al., "Structural basis of carbohydrate recognition by the lectin LecB from pseudomonas aeruginosa," J. Mol. Biol., 2003, 331, 861-870.
Mansour, M.H., et al., "Distinct binding patterns of fucose-specific lectins from Biomphalaria alexandrina and lotus tetragonolobus to murine lymphocyte subsets," Immunobiology, 2005, 210, 335-348.
Marrero, J.A., et al., "GP73, a resident golgi glycoprotein, is a novel serum marker for hepatocellular carcinoma," J. Hepatol. 2005, 43, 1007-1012.
Mehta, A.S. et al., "Increased Levels of Galactose-Deficient Anti-Gal Immunoglobulin G in the Sera of Hepatitis C Virus-Infected Individuals with Fibrosis and Cirrhosis," J. Virology, 2008, 82, 1259-1270.
Miyoshi, E., et al., "The alphal-6-fucosyltransferase gene and its biological significance," Biochimica Et Biophysica Acta, Amsterdam, NL, 1999, 1473(1), 9-20.
Naitoh, A., et al., "Highly enhanced fucosylation of serum glycoproteins in patients with hepatocellular carcinoma," J. Gastroenterol. Hepatol., 1999, 14, 436-445.
Nguyen, M.H., et al., "Racial differences in effectiveness of α-fetoprotein for diagnosis of hepatocellular carcinoma in hepatitis C virus cirrhosis," Hepatology, 2002, 36, 410-417.
Nimmerjahn, F. et al., "Agalactosylated IgG antibodies depend on cellular Fc receptors for in vivo activity," 2007 Proc Natl Acad Sci U S A 104:8433-7.
Oka H et al., "Prospective study of α-fetoprotein in cirrhotic patients monitored for development of hepatocellular carcinoma," Hepatology, 1994, 19, 61-7.
Pateron, D., et al., "Prospective study of screening for hepatocellular carcinoma in Caucasian patients with cirrhosis," J. Hepatol., 1994, 20, 65-71.
Rattan S.I.S., et al., "Protein Synthesis: Posttranslational Modifications and Aging,"Ann. NY Acad. Sci., 1992, 663, 48-62.
Roy, S.S., et al., "Detection of root mucilage using an anti-fucose antibody," Ann. Botany, 2002, 89, 293-299.
Rudd, P.M. et al., "Glycoproteins: Rapid Sequencing Technology for N-linked and GPI Anchor Glycans," 1999 Biotechnol Genet Eng Rev 16:1-21.
Rudd, P.M. et al., "Rapid, sensitive sequencing of oligosaccharides from glycoproteins," 1997 Curr Opin Biotechnol 8:488-97.
Seifter, S., et al, "Analysis for Protein Modifications and Nonprotein Cofactors," Methods Enzymol. 1990, 182, 626-646.
Srikrishna G ,et al., "Fucoseβ-1-ser is a new type of glycosylation: using antibodies to identify a novel structure in *dictyostelium discoideum* and study multiple types of fucosylation during growth and development," Glycobiology, 1998, 8, 799-811.
Tockman, M.S. et al., "Considerations in Bringing a Cancer Biomarker to Clinical Application," Cancer Res., 1992, 52, 2711s-2718s.
Zoli, M., et al., "Efficacy of a surveillance program for early detection of hepatocellular carcinoma," Cancer, 1996, 78, 977-983.
Chambers et al., "Abnormally fucosylated haptoglobin as a marker for alcoholic liver disease but not excessive alcohol consumption or non-alcoholic liver disease," Clinica Chimica Acta, Oct. 1993, 219(1-2), 177-182.

(56) References Cited

OTHER PUBLICATIONS

Thompson et al., "Abnormally-fucosylated haptoglobin: a cancer marker for tumour burden but not gross liver metastasis," Br. J. Cancer, Aug. 1991, 64(2), 386-390.
Du et al., "Differential binding of serum glycoproteins to lectins during hepatic regeneration in hepatocellular carcinoma and fulminant hepatic failure," Clinical Science, Jun. 1990, 78(6), 551-555.
Comunale, M.A., et al., "Identification and Development of Fucosylated Glycoproteins as Biomarkers of Primary Hepatocellular Carcinoma," Journal of Proteome Research, Feb. 2009, 8(2), 595-602.
Matsumoto et al., "Alteration of asparagine-linked glycosylation in serum transferrin of patients with hepatocellular carcinoma," Clin. Chim. Acta., Jan. 14, 1994, 224(1), 1-8.
Ryden et al, "Diagnostic Accuracy of Alpha(1)-acid Glycoprotein Fucosylation for Liver Cirrhosis in Patients Undergoing Hepatic Biopsy", Clinical Chemistry, Dec. 2002, 48(12), 2195-2201.
Steel et al, "A Proteomic Approach for the Discovery of Early Detection Markers of Hepatocellular Carcinoma", Disease Markers, 2001, 17(3),179-89.
Brinkman-van der Linden, et al., "Inflammation-Induced Expression of Sialyl Lewis is Not Restricted to a1-Acid Glycoprotein but also Occurs to a Lesser Extent on a1-Antichymotrypsin and Haptoglobin", Glycoconjugate Journal, 1998, vol. 15, 177-182.
Gravel, et al, "Identification of Glycoproteins on Nitrocellulose Membranes using lectin Blotting", The Protein Protocols Handbook, 1996, Editor John M. Walker, Chapter 97, pp. 603-617.
Guo, et al., "Repeated Immunization Induces the Increase in Fucose Content on Antigen-Specific IgG N-linked Oligosaccharides", Clinical Biochemistry, Feb. 2005, vol. 38, pp. 149-153.
Matsumara, et al., "Carbohydrate Binding Specificity of a Fucose-Specific Lectin from Aspergillus Oryzae", Journ. of Biological Chemistry, Feb. 2007, vol. 282, 15700-15708.
Miyamoto, et al., "Lectin Histochemistry in Rat Liver Fibrosis Induced by Heterologous Serum Sensitization", J. Vet Med. Sci., Apr. 1997, pp. 681-687.
Wang et al.; "Novel Fucosylated Biomarkers for the Early Detection of Hepatocellular Carcinoma"; Cancer Epidemiol Biomarkers and Prevention; vol. 18 No. 6; Jun. 2009; p. 1914-1921.
European Patent Application No. 15186776.9; Extend Search Report; dated May 25, 2016; 10 pages.

\* cited by examiner

DIAGNOSIS OF LIVER PATHOLOGY THROUGH ASSESSMENT OF PROTEIN GLYCOSYLATION

CROSS-REFERENCE TO RELATED APPLICATIONS

This application is the National Stage of International Application No. PCT/US2006/017478 filed May 5, 2006, which claims the benefit of U.S. Provisional Application No. 60/677,941, filed May 5, 2005, the disclosure of which is incorporated herein by reference in its entirety.

GOVERNMENT SUPPORT

This invention was made with government support under Grant Numbers R33CA94340 and U01 CA84951 awarded by the NCI. The government has certain rights in the invention.

FIELD OF THE INVENTION

The invention relates generally to the field of immunodiagnostics. More specifically, the invention relates to methods and kits for rapid and accurate diagnosis of liver diseases such as hepatocellular carcinoma, hepatitis, and cirrhosis via the detection of specific fucosylated glycoproteins identified as being associated with liver pathologies.

BACKGROUND OF THE INVENTION

Various publications, including patents, published applications, technical articles and scholarly articles are cited throughout the specification. Each of these cited publications is incorporated by reference herein, in its entirety.

The liver is the largest gland in the body, and plays a vital role in, among other things, digestion, metabolism of carbohydrates, lipids, and proteins, storage of vitamins, minerals, and carbohydrates, production of blood clotting factors, destruction of bacteria in the blood, and detoxification of the body from endogenous and exogenous substances. Given the liver's broad spectrum of functions, diseases and pathologies of the liver can have wide-ranging systemic effects on the body.

One common liver pathology is hepatocellular carcinoma (HCC). HCC ranks fifth of the most common cancers in the world, and is the third leading cause of cancer death (El-Serag H et al. (2001) Hepatology 33:62-5; and, Block T et al. (2003) Oncogene 22:5093-107). The primary etiology for HCC is viral infection, particularly, infection with hepatitis B virus (HBV) and hepatitis C virus (HCV) (Brechot C (1996) Baillieres Clin. Gastroenterol. 10:335-73). HCC can lead to liver cirrhosis. In addition, cirrhosis is a risk factor for HCC (Ikeda K et al. (1993) Hepatology 18:47-53).

Liver cirrhosis is characterized by, among other things, extensive fibrosis, hepatocyte necrosis, collapse of the supporting reticulin network, and extensive deposition of connective tissue. There are multiple etiologies for liver cirrhosis, including viral hepatitis, alcohol abuse, genetics (e.g., Wilson's Disease), venous thromboses in Budd-Chiari Syndrome, and autoimmunity (e.g., Primary Biliary Cirrhosis). Cirrhosis of the liver is irreversible, and if not controlled, can lead to liver failure. In fact, liver cirrhosis is a leading cause of death among adults in the United States, and throughout the world.

It is important that liver diseases such as HCC be detected early in order to provide the patient with the full range of therapeutic options and ultimately improve patient prognosis (Hoofnagle, J H et al. (1997) N. Engl. J. Med. 336:347-56). Furthermore, it is equally important that conditions that predispose to HCC and other liver diseases, for example, cirrhosis, and HBV and HCV infection, be detected early for effective treatment, and for the prevention of the onset of HCC. Unfortunately, many liver diseases, including HBV and HCV infection, can be asymptomatic for many years In general, liver diseases are diagnosed and monitored by serologic testing, and liver function testing, as well as by physical examination of the patient. In addition, as there is an apparent correlation between elevated expression of alpha-fetoprotein (AFP) and the presence of HCC, screening for AFP is often carried out as a matter of course in cases of suspected liver disease (Buamah P K et al. (1984) Clin. Chim. Acta 139:313-6). However, AFP suffers from several major drawbacks insofar as it can be expressed in the absence of disease, leading to false positive diagnoses, and it is not found to be elevated in up to 50% of liver cancer cases, leading to false negative diagnoses (Nguyen M H et al. (2002) Hepatology 36:410-7). Moreover, the predictive value of AFP substantially diminishes with respect to its capacity to identify early stage HCC (Oka H et al. (1994) Hepatology 19:61-7; Pateron D et al. (1994) J. Hepatol. 20:65-72; and, Zoli M et al. (1996) Cancer 78:977-83).

Thus, more rapid, accurate, and reliable means for the diagnosis of liver diseases that are minimally invasive to the patient, and can be readily and cost-effectively administered to all patients suspected of having liver disease are needed. In addition, there is a need for diagnostic tests that can detect the presence of disease in its incipient or early stages to facilitate effective prophylactic treatment of the patient.

SUMMARY OF THE INVENTION

The present invention features methods for diagnosing pathologies of the liver or biliary system. Generally, the methods comprise obtaining a test sample such as a biological fluid from a subject suspected of having a pathology of the liver or biliary system, quantifiably detecting glycosylation on proteins in the sample, and then comparing the detected glycosylation with reference values for glycosylation of such proteins. The reference values are established from subjects with no liver or biliary system pathology and from subjects with known liver pathologies. Either or both reference values can be compared with the detected glycosylation levels, and the comparison will reveal the presence or absence of the pathology of the liver or biliary system.

The inventive methods can be applied to detect any liver pathology, but are preferably applicable to detect hepatocellular carcinoma, hepatitis, cirrhosis, or combinations thereof. The preferred glycosylation that is detected is fucosylation. Any fucosylated protein that is now or is identified in the future as being associated with liver or biliary system pathology can be used as the target analyte. Non-limiting examples of fucosylated proteins that have been identified include GP-73, Hemopexin, HBsAg, hepatitis B viral particle, alpha-acid-glycoprotein, alpha-1-antichymotrypsin, alpha-1-antichymotrypsin His-Pro-less, alpha-1-antitrypsin, Serotransferrin, Ceruloplasmin, alpha-2-macroglobulin, alpha-2-HS-glycoprotein, alpha-fetoprotein, Haptoglobin, Fibrinogen gamma chain precursor, immunoglobulin (including IgG, IgA, IgM, IgD, IgE, and the like), APO-D, Kininogen, Histidine rich glycoprotein, Complement factor 1 precursor, complement factor I heavy chain, complement factor I light chain, Complement C1s, Complement factor B precursor, complement factor B Ba fragment, Complement factor B Bb fragment, Complement C3 precursor, Complement C3 beta chain, Complement C3 alpha chain, C3a anaphylatoxin, Complement, C3b alpha' chain, Complement C3c fragment, Complement C3dg fragment, Complement C3g fragment, Complement C3d fragment, Complement C3f fragment, Complement C5, Complement C5 beta chain, Complement C5 alpha chain, C5a anaphylatoxin, Complement C5 alpha' chain, Complement C7, alpha-1 B glycoprotein, B-2-glycoprotein, Vitamin D-binding protein, inter-alpha-trypsin inhibitor heavy chain H2, Alpha-1B-glycoprotein, Angiotensinogen precursor, Angiotensin-1, Angiotensin-2, Angiotensin-3, GARP protein, beta-2-glycoprotein, Clusterin (Apo J), Integrin alpha-8 precursor glycoprotein, integrin alpha-8 heavy chain, Integrin alpha-8 light chain, hepatitis C viral particle, eIF-5, kininogen, HSP33-homolog, lysyl endopeptidase and Leucine-rich repeat-containing protein 32 precursor.

The detection can proceed via any assay suitable in the art. The detection reagent can directly label the glycosyl moieties, for example, via carbohydrate specific chemicals or dyes, or via labeled lectins, labeled carbohydrate binding proteins, or labeled antibodies. The detection reagent can be a secondary reagent, for example, by first capturing the target analyte and then contacting the capture reagent-target complex with a labeled secondary reagent. Detection can proceed by separating glycosyl moieties from the proteins prior to the quantifiable detection of glycosylation. Detection can proceed by separating glycoproteins from the test sample prior to the quantifiable detection of glycosylation.

The invention also feature novel methods for detecting glycosylated proteins in a sample. Such methods comprise contacting a sample with a lectin and detecting the lectin-glycosylated protein complex. The glycosylated proteins can be fucosylated proteins. The lectin can be directly coupled to a detectable moiety, or detection can proceed via a secondary reagent that specifically binds to the lectin, such as an anti-lectin antibody. The methods can comprise first contacting the sample with an antibody to capture target glycosylated proteins in the sample, for example, an antibody specific for the glycoproteins exemplified herein.

Also featured in the present invention are kits for diagnosing pathologies of the liver or biliary system. The kits comprise a reagent that specifically binds to glycosyl moieties, preferably fucosyl moieties. The reagent can be labeled with a detectable moiety, or can be a chemical that specifically labels glycosyl moieties, preferably fucosyl moieties. If the reagent supplied with the kits is not coupled to a detectable moiety, the kit can further comprise a detection reagent that specifically recognizes the reagent-glycoprotein complex, the detection reagent being coupled to a detectable moiety. The kits further include instructions for using the kit in a method to diagnose a pathology of the liver or biliary system.

BRIEF DESCRIPTION OF THE DRAWINGS

FIG. 1 shows an example of glycoforms. Normally, liver cells produce glycoproteins that contain the carbohydrate structure shown in panel A. This is referred to as a biantennary glycan (A2G2). In HCC, the liver cells attach a fucose residue to the glycan chain resulting in a fucosylated glycoprotein (glycoform, referred to with the Fc prefix). Examination of all proteins having a specific carbohydrate chain is referred to as targeted glycoproteomics. Abbreviations in the figure are as follows: N-acetylglucosamine (GlcNAc); mannose (Man); galactose; (Gal); sialic acid (NeuNAc); Fucose (Fuc).

FIG. 2 shows the level of the FcA2G2 glycan in people as a function of time. (A) The level of the FcA2G2 structure in a patient either before (upper panel) or after (lower panel) the diagnosis of cancer. As this figure shows, the level of the FcA2G2 structure increases from 7.23% of the total glycan pool to over 13% of the total glycan pool after the diagnosis of cancer. (B) Levels of the FcA2G2 structure in 8 individuals either before or after the diagnosis of cancer. On the graph, the Y axis is the percentage of FcA2G2 structure in each individual as a function of total released glycan. The X axis is the sample number.

FIG. 3 shows the lectin ELISA design utilized for Fc-AFP and Fc-Kininogen. Periodate oxidized antibody was used as the capture antibody and the level of fucosylated protein determined by an alkaline phosphate conjugated lectin (LcH) using a calorimetric substrate (5-bromo-4-chloro-3-indolyl phosphate/nitroblue tetrazolium (BCIP/NBT)).

DETAILED DESCRIPTION OF ILLUSTRATIVE EMBODIMENTS

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Definitions

The following abbreviations may be used in the specification and examples: HAV, hepatitis A virus; HBV, hepatitis B virus; HCV, hepatitis C virus, HDV, hepatitis D virus; HEV, hepatitis E virus; HFV, hepatitis F virus; HGV, hepatitis G virus; AFP, alpha-fetoprotein; HCC, hepatocellular carcinoma; HPLC, high performance liquid chromatography; Fc, fucosylated.

As used in this specification and the appended claims, the singular forms "a", "an" and "the" include plural referents unless the content clearly dictates otherwise. Thus, for example, reference to "a cell" includes a combination of two or more cells, and the like.

"Pathology" means any condition that is a deviation from the normal or healthy state.

The term "biliary system" refers to the organs and duct system that create, transport, store, and release bile into the small intestine. The term encompasses the liver, gallbladder, and bile ducts: the cystic duct, hepatic duct, common hepatic duct, common bile duct, and pancreatic duct.

Diseases and pathologies of the liver or biliary system abound. Non-limiting examples of liver or biliary diseases include Alagille Syndrome, Alcoholic Liver Disease, Alpha-1-antityrpsin Deficiency, Autoimmune Hepatitis, Budd-Chiari Syndrome, Biliary Atresia, Byler Disease, Caroli Disease, Cholangiocarcinoma, Crigler-Najjar Syndrome, Drug- or Alcohol-induced Hepatitis, Dubin-Johnson Syndrome, Fatty Liver/Steatosis, Gilbert Syndrome, Hemangioma, Hemohromatosis, Hepatitis Virus A, B, C, D, E, and G, Hepatocellular Carcinoma, Hyperbilirubinemia, Primary Biliary Cirrhosis, Protoporphyria, Rotor Syndrome, Sclerosing Cholangitis, and Wilson Disease.

A common liver pathology is cirrhosis. Cirrhosis of the liver is characterized by, among other things, widespread nodule formation in the liver, extensive fibrosis, hepatocyte necrosis, collapse of the supporting reticulin network, extensive deposition of connective tissue, diminished blood flow through the liver, decreased bilirubin secretion, jaundice, and the disruption of normal liver biochemical functions. There are multiple etiologies for liver cirrhosis. More common causes include damage done to the liver by ingestion of alcohol, drugs, or toxins, especially as in the case of alcoholic liver disease. Cirrhosis may also be virally induced by, for example, different strains of the hepatitis virus, inherited (e.g., Wilson's Disease, and hemochromatosis), induced by chronic disease or disruption of the bile ducts, by parasitic infections (e.g., schistosomiasis), by excess iron absorption, by autoimmunity (e.g., Primary Biliary Cirrhosis), or by liver inflammation resulting from fatty liver disease, among others.

"Hepatitis" refers to any clinically significant inflammation of the liver or biliary system, regardless of etiology. "Acute hepatitis" refers to any short term (less than six months) or initial-stage liver inflammation, such as the initial stages of hepatitis virus infection. "Chronic hepatitis" refers to any inflammation of the liver persisting six months or longer. "Infectious hepatitis" refers to any inflammation of the liver that can be transmitted to others. Typically, infectious hepatitis is caused by a microorganism such as a virus (e.g., HAV, HBV, HCV, HDV, HEV, HFV, HGV, cytomegalovirus, Epstein-Barr virus, herpes simplex virus (HSV), and Varicella-Zoster virus, etc.), bacteria, protozoan, or yeast. "Non-infectious hepatitis" refers to any inflammation of the liver that cannot be transmitted to others, such as alcoholic hepatitis, autoimmune hepatitis, toxic/drug induced hepatitis, and granulomatus hepatitis, and the like.

"Etiology" means the cause or origin of a disease, disorder, or pathology.

"Antibodies" as used herein includes polyclonal and monoclonal antibodies, chimeric, single chain, and humanized antibodies, as well as antibody fragments (e.g., Fab, Fab', F(ab')$_2$ and F$_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al (Eds.), ANTIBODIES A LABORATORY MANUAL; Cold Spring Harbor Laboratory; Cold Spring Harbor, N.Y. (1988), Chapter 6.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods.

"Post-translational modification" refers to any chemical modification of a polypeptide after it is produced. Commonly, a post-translational modification involves attaching at least one moiety to the polypeptide chain, however, post-translations modification can be cleavage of the polypeptide chain, proteolytic processing, the formation of disulfide bonds, and the like. Non-limiting examples of post-translational modifications include, glycosylation, phosphorylation, acylation, acetylation, methylation, sulfonation, prenylation, isoprenylation, ubiquitination, biotinylation, formylation, citrullination, myristolation, ribosylation, sumoylation, gamma carboxylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, demethylation, formation of covalent cross-links, formation of cystine, formation of pyroglutamate, GPI anchor formation, hydroxylation, iodination, methylation, oxidation, proteolytic processing, racemization, selenoylation, sulfation, transfer-RNA mediated addition of amino acids to proteins such as arginylation, and the like. See, for instance, Proteins—Structure and Molecular Properties, 2nd Ed., T. E. Creighton, W.H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al, (1990) Analysis for Protein Modifications and Nonprotein Cofactors, Methods Enzymol. 182:626-46 and Rattan et al (1992) Protein Synthesis: Posttranslational Modifications and Aging, Ann. NY Acad. Sci. 663:48-62.

As used herein, "glycosylation" refers to the chemical attachment of at least one saccharide moiety to a molecule such as a polypeptide. Glycosylation can be n-linked or o-linked.

"Fucosylation" refers to the chemical attachment of at least one fucose moiety to a molecule such as a protein. A "fucosylated" polypeptide is a polypeptide with at least one fucose moiety attached.

"Core glycosylation" refers to the addition of glycosyl moieties to the core N-acetylglucosamine. "Core fucosylation" refers to the addition of a fucose residue to the core N-acetylglucosamine. All N-linked glycan structures have a common structure, referred to as the core, containing three mannose, and two N-acetylglucosamine residues.

A "glycoform" refers to a group of proteins having the identical amino acid sequence but having different carbohydrate moieties.

It has been discovered in accordance with the present invention that there is a correlation with the incidence of liver disease such as hepatocellular carcinoma, hepatitis virus infection, and cirrhosis and an increase in the level of core fucosylation. Analysis of the serum proteome from patients with liver disease revealed over fifty glycoproteins that demonstrate increased fucosylation relative to healthy controls, thereby revealing that increased protein fucosylation is indicative of liver disease state. Accordingly, in one aspect, the invention features methods to diagnose a pathology of the liver or biliary system in a patient suspected of having a pathology of the liver or biliary system. Such methods comprise obtaining a test sample from a patient suspected of having a pathology of the liver, and quantifiably detecting post-translational modifications on proteins in the test sample, wherein modulated levels of the post-translational modifications relative to reference values for post-translational modifications for such proteins indicates the presence or absence of a pathology of the liver.

A test sample can be obtained from any location in a patient in which post-translationally modified proteins indicative of a condition of the liver are likely to be found. For example, a test sample can be obtained from biological fluids such as tears, saliva, mucous, whole blood, serum, plasma, urine, bile, and the like. A test sample could also be obtained from specific cells or tissue, or from any secretions or exudate. For example, a biopsy of cells or tissues from the liver or biliary system can serve as a test sample. Preferably, the test sample is obtained from peripheral blood.

In one preferred embodiment, detection of the post-translational modification can be carried out by detecting a polypeptide-moiety complex. In another preferred embodiment, detection of the post-translational modification can be carried out by separating the polypeptide and moiety, and detecting the moiety.

Detection of the polypeptide-moiety complex can be carried out using a reagent that specifically recognizes the moiety, the particular class of moiety, or the moiety as a complex with the polypeptide. Suitable detection reagents will be apparent to those of skill in the art, non-limiting examples of which are described below. The reagent can comprise multiple molecules each having specificity for a different target moiety, thereby resulting in multiple reagent-target interactions.

Antibodies can be used as the reagent. Any antibody that specifically binds to the target moiety of interest can be used in the present invention. Monoclonal and/or polyclonal antibodies can be used, from whatever source produced, as can recombinant antibodies such as single chain antibodies and phage-displayed antibodies, as well as chimeric and humanized antibodies. Antigen binding fragments of antibodies such as the Fab or Fv can also be used.

In some embodiments, the antibodies specifically recognize glycoproteins. Preferably, the antibodies specifically recognize carbohydrate moieties, including mono- and polysaccharides. More preferably, the antibodies specifically recognize fucose moieties. Antibodies capable of specifically recognizing fucose have been described. See, e.g., Roy S S et al. (2002) Ann. Bot. 89:293-9; and, Srikrishna G et al. (1998) Glycobiology 8:799-811. In the alternative, antibodies can also be raised to various moieties, including fucose, and used in the invention. Methods for raising and purifying antibodies are well known in the art. In addition, monoclonal antibodies can be prepared by any number of techniques that are known in the art, including the technique originally developed by Kohler and Milstein (1975) Nature 256:495-497.

Other proteins that have carbohydrate recognition domains can also be used as the reagent in the present invention. Proteins having carbohydrate recognition domains have been described, see, e.g., Bouyain S et al. (2002) J. Biol. Chem. 277:22566-72 (*Drosophila melanogaster* protein CG2958 that recognizes fucose).

In particularly preferred embodiments, lectins are used as the reagent. The lectins can be obtained from any organism, including plants, animals, yeast, bacteria, protozoans, and the like. Purified lectins are commercially available, see, e.g., Sigma-Aldrich catalog (St. Louis, Mo.). Lectins can also be isolated from their naturally occurring source, or recombinantly expressed and purified, by means that are well-known to those of skill in the art. The lectin can, but need not be specific for a particular carbohydrate moiety. Fucose-specific lectins have been described. See, e.g., Mansour M H et al (2005) Immunobiology. 210:335-48; Amano K et al. (2003) Biosci. Biotechnol. Biochem. 67:2277-9; Loris R et al. (2003) J. Mol. Biol. 331:861-70; and, Ishida H et al. (2002) Biosci. Biotechnol. Biochem. 66:1002-8. It is contemplated that future-identified lectins are suitable for use in the present invention.

Proteins with lectin-like domains are also suitable for use in the present invention. Proteins with lectin-like domains are known in the art. See, e.g., Drickamer K (1999) Curr. Opin. Struct. Biol. 9:585-90.

Nucleic acid-based alternatives to lectins can also be used. Such reagents, termed aptamers, take advantage of the huge conformational flexibility of single stranded nucleic acids. From large pools of randomized short nucleic acids, individual molecules with high affinities for numerous non-nucleic acid ligands have been isolated by iterative selection. Advantages of the glycan-binding "lectamer" reagents are that leached DNAs are unlikely to confuse or interfere with downstream analyses. Lectamers can function under uniform binding conditions (pH, ionic strength). Synthetic nucleic acids can be prepared in various derivatized forms (e.g., terminally biotinylated). Target glycans are not limited by existing lectin specificities, substantially expanding existing fractionation and analytical capabilities.

Any polypeptide on which post-translational modifications are modulated upon the onset or progression of a pathology of the liver can be used in the inventive diagnostic assays. Non-limiting examples of such polypeptides that have been characterized thus far include GP-73, Hemopexin, HBsAg, hepatitis B viral particle, alpha-acid-glycoprotein, alpha-1-antichymotrypsin, alpha-1-antichymotrypsin His-Pro-less, alpha-1-antitrypsin, Serotransferrin, Ceruloplasmin, alpha-2-macroglobulin, alpha-2-HS-glycoprotein, alpha-fetoprotein, Haptoglobin, Fibrinogen gamma chain precursor, immunoglobulin (including IgG, IgA, IgM, IgD, IgE, and the like), APO-D, Kininogen, Histidine rich glycoprotein, Complement factor 1 precursor, complement factor I heavy chain, complement factor I light chain, Complement C1s, Complement factor B precursor, complement factor B Ba fragment, Complement factor B Bb fragment, Complement C3 precursor, Complement C3 beta chain, Complement C3 alpha chain, C3a anaphylatoxin, Complement, C3b alpha' chain, Complement C3c fragment, Complement C3dg fragment, Complement C3g fragment, Complement C3d fragment, Complement C3f fragment, Complement C5, Complement C5 beta chain, Complement C5 alpha chain, C5a anaphylatoxin, Complement C5 alpha' chain, Complement C7, alpha-1 B glycoprotein, B-2-glycoprotein, Vitamin D-binding protein, Inter-alpha-trypsin inhibitor heavy chain H2, Alpha-1B-glycoprotein, Angiotensinogen precursor, Angiotensin-1, Angiotensin-2, Angiotensin-3, GARP protein, beta-2-glycoprotein, Clusterin (Apo J), Integrin alpha-8 precursor glycoprotein, Integrin alpha-8 heavy chain, Integrin alpha-8 light chain, hepatitis C viral particle, elf-5, kininogen, HSP33-homolog, lysyl endopeptidase and Leucine-rich repeat-containing protein 32 precursor. It is contemplated that additional post-translationally modified proteins that are found to be correlated with a liver pathology can be used in the inventive methods.

The reagent can be directly labeled with a detectable moiety. In the alternative, a secondary reagent that specifically recognizes the primary reagent, which is labeled with a detectable moiety is used. The secondary reagent can be any molecule, and is preferably an antibody. The secondary reagent is labeled with a detectable moiety. Detectable moieties contemplated for use in the invention include, but are not limited to, radioisotopes, fluorescent dyes such as fluorescein, phyocoerythrin, Cy-3, Cy5, allophycocyanin, DAPI, Texas red, rhodamine, Oregon green, lucifer yellow, and the like, green fluorescent protein, red fluorescent protein, Cyan Fluorescent Protein, Yellow Fluorescent Protein, Cerianthus Orange Fluorescent Protein, alkaline phosphatase, β-lactamase, chloramphenicol acetyltransferase, adenosine deaminase, aminoglycoside phosphotransferase ($neo^r$, $G418^r$) dihydrofolate reductase, hygromycin-B-phosphotransferase, thymidine kinase, lacZ (encoding α-galactosidase), and xanthine guanine phosphoribosyltransferase, Beta-Glucuronidase, Placental Alkaline Phosphatase, Secreted Embryonic Alkaline Phosphatase, or Firefly or Bacterial Luciferase. Enzyme tags are used with their cognate substrate. As with other standard procedures associated with the practice of the invention, skilled artisans will be aware of additional labels that can be used. In some embodiments, the reagent or secondary reagent are coupled to biotin, and contacted with avidin or strepatvidin having a detectable moiety tag.

In some embodiments, the moiety attached to the polypeptide by post-translational modification can be directly labeled and detected, thereby obviating the need for a labeled reagent that specifically recognizes a particular moiety as well as any need for a labeled secondary reagent. In some embodiments, the moiety attached to the polypeptide by post-translational modification can be separated from the polypeptide and directly labeled and detected. For example, and not by way of limitation, carbohydrates and carbohydrate moieties can be directly labeled using various methods that are known in the art. Carbohydrate and carbohydrate moiety labeling kits are commercially available. Carbohydrate and carbohydrate moieties can also be biotinlyated and labeled with avidin- or streptavidin-conjugated detectable moieties, such as those described herein. Non-limiting examples of reagents that can directly label oligosaccharides include 2-aminobenzamide and 2-aminobenzoic acid.

Post-translationally attached moieties can be separated from a polypeptide by any means suitable in the art, including chemically, for example by treatment with hydrazine or acids such as hydrofluoric acid or trifluoromethanesulfonic acid, enzymatically, for example by treatment with N-glycosidase such as PNGase F, O-glycosidase, endoglycosidases, or exoglycosidases, or by physical means. Commercially available kits are available for removing post-translational modifications, including deglycosylation. Chemical bases such as hydrazine, or chemical reagents that lead to beta-elination reactions can also be used in deglysosylation reactions. Other techniques and reagents will be appreciated by those of skill in the art, and are contemplated to be within the scope of the present invention.

In some embodiments, the separated moieties are purified prior to labeling or detection. Solid or liquid phase extraction techniques, which are known in the art, can be used to purify the separated moieties for further analysis.

Reference values can be those established for a particular liver pathology, or those established for healthy subjects, or both. In addition, the present invention contemplates that screening of test samples using the inventive methods will reveal additional post-translationally modified proteins, and the particular type and level of post-translational modification of said proteins, which correlate with disease state or healthy state. Using this information, these identified proteins can serve as additional reference values against which test samples can be compared.

A variety of assay formats can be used to carry out the inventive methods, and to quantitatively detect post-translational modifications of proteins. Immunoassays are one preferred assay, and include but are not limited to ELISA, radioimmunoassays, competition assays, Western blotting, bead agglomeration assays, lateral flow immunoassays, immunochromatographic test strips, dipsticks, migratory format immunoassays, and the like. Other suitable immunoassays will be known to those of relevant skill in the art. Microscopy can also be used. In some embodiments, chromatography is the preferred assay. High performance liquid chromatography (HPLC) is particularly preferred. In some embodiments, mass spectroscopy is the preferred assay. In some embodiments, gel electrophoresis coupled with densitometry is used as the assay.

The general format of the assays involve contacting the reagent with a test sample containing the analytes of interest, namely the post-translationally modified proteins, which may be distinguished from other components found in the sample. Following interaction of the analyte with the reagent, the system can be washed and then directly detected or detected by means of a secondary reagent as exemplified herein.

In some preferred embodiments, the reagent is immobilized on a solid support. In other preferred embodiments, the test sample, or molecules separated or purified from the test sample, such as post-translationally modified polypeptides, are immobilized on a solid support. Techniques for purification of biomolecules from samples such as cells, tissues, or biological fluid are well known in the art. The technique chosen may vary with the tissue or sample being examined, but it is well within the skill of the art to match the appropriate purification procedure with the test sample source.

Examples of suitable solid supports include, but are not limited to, glass, plastic, metal, latex, rubber, ceramic, polymers such as polypropylene, polyvinylidene difluoride, polyethylene, polystyrene, and polyacrylamide, dextran, cellulose, nitrocellulose, pvdf, nylon, amylase, and the like. A solid support can be flat, concave, or convex, spherical, cylindrical, and the like, and can be particles, beads, membranes, strands, precipitates, gels, sheets, containers, wells, capillaries, films, plates, slides, and the like. The solid support can be magnetic, or a column.

As the various post-translationally modifications associated with the presence of a liver pathology identified to date can be present at detectable levels within normal subjects (those without a liver pathology), it may be necessary to quantitatively measure the levels of each marker being analyzed in the diagnostic assay. In such cases, modulation of levels of the modifications relative to standards/controls will be indicative of the presence of a liver pathology. Normal expression levels of the various modifications can be empirically determined according to any of various techniques that are known in the art. The normal expression levels can serve as a standard against which the expression levels in suspected liver pathology patients can be compared. Significant deviation (positive or negative) over expected normal expression levels of liver pathology-associated modifications is indicative of the presence of a liver pathology in the patient. Similarly, the expression levels observed in confirmed liver pathology patients can also serve as a standard against which the expression levels in suspected liver pathology patients can be compared. Similar levels of expression of the liver pathology-associated markers between the known patient and suspected patient is indicative of the presence of a pathology in the patient. In such cases, it is expected that the expression level of the modifications in both the known and suspected samples will significantly deviate from the level of expression present in healthy subjects.

The present methods have applicability to diagnose a liver pathology in any animal. Preferably, the methods are utilized in mammals such as dogs, cats, horses, cows, pigs, rabbits, donkeys, sheep, mice, and rats. Most preferably, the methods are utilized in humans.

Also featured in the present invention are devices to diagnose a pathology of the liver or biliary system in a patient suspected of having a pathology of the liver. The devices comprise a reagent specific for a post-translationally attached moiety associated with the presence of a liver pathology, which is preferably coupled to a solid support. The devices are capable of use in any assay, particularly those described and exemplified herein, wherein the assay can quantifiably detect the presence of the moiety associated with a liver pathology, and wherein modulated levels of the expression of the moiety relative to a standard indicates the presence of a pathology of the liver.

The reagents for use in the devices can comprise a single molecule that can form a complex with a single target, or multiple targets, for example, a multimeric fusion protein with multiple binding sites for different targets. The reagent can comprise multiple molecules each having specificity for a different target. In preferred embodiments, the reagent is comprised of proteins. In some preferred embodiments, the reagent is of antibodies, and any antibody that specifically binds to the target marker of interest can be used in the devices. In some preferred embodiments, the reagent is comprised of carbohydrate recognition domains. In highly preferred embodiments, the reagent is comprised of lectins or proteins with lectin domains, as exemplified herein.

The solid support to which the reagent is coupled can be any solid support described herein. The reagent can be immobilized on the solid support by any means suitable in the art, such as adsorption, non-covalent interactions such as hydrophobic interactions, hydrophilic interactions, van der Waals interactions, hydrogen bonding, and ionic interactions, electrostatic interactions, covalent bonds, or by use of a coupling agent. Coupling agents include glutaraldehyde, formaldehyde, hexamethylene diisocyanate, hexamethylene diisothiocyanate, N,N'-polymethylene bisiodoacetamide, N,N'-ethylene bismaleimide, ethylene glycol bissuccinimidyl succinate, bisdiazobenzidine, 1-ethyl-3-(3-dimethylaminopropyl) carbodiimide, succinimidyl 3-(2-pyridyldithio) propionate (SPDP), N-succinimidyl 4-(N-maleimidomethyl)cyclohexane-1-carboxylate (SMCC), N-sulfosuccinimidyl 4-(N-maleimidomethyl)-cyclohexane-1-carboxylate, N-succinimidyl (4-iodoacetyl)-aminobenzoate, N-succinimidyl 4-(1-maleimidophenyl)butyrate, N-(epsilon-maleimidocaproyloxy)succinimide (EMCS), iminothiolane, S-acetylmercaptosuccinic anhydride, methyl-3-(4'-dithiopyridyl)propionimidate, methyl-4-mercaptobutyrylimidate, methyl-3-mercaptopropionimidate, N-succinimidyl-5-acetylmercaptoacetate, avidin, streptavidin, biotin, *Staphylococcous aureus* protein A, and the like.

Sites on the solid support not coupled with the capture reagent can be blocked to prevent non-specific binding of marker molecules to the solid support. Blocking reagents and procedures are well known in the art.

Also featured in accordance with the present invention are kits for diagnosing pathology of the liver or biliary system. In one embodiment, the kits include a reagent that specifically interacts with glycosyl moieties, and instructions for using the kit in a method for diagnosing pathology of the liver. The reagent can be a molecule that directly labels oligosaccharides such as 2-aminobenzamide, or can be a molecule that is coupled to a detectable moiety as described herein. In some embodiments, the kits further comprise a secondary reagent that specifically recognizes the primary reagent, which is labeled with a detectable moiety. The kits can also include positive and negative controls.

In preferred embodiments, the reagent is comprised of antibodies, and any antibody that specifically binds to the glycosyl moiety of interest can be used in the devices. In more preferred embodiments, the reagent is comprised of proteins that can specifically interact with carbohydrates. In still more preferred embodiments, the reagent is comprised of lectins. The preferred glycosyl moiety is fucose.

In some embodiments, the kits further include a solid support to immobilize the reagent or the analyte from the test sample isolated from the patient. The solid support can be any solid support described herein. The kit may further include coupling agents to facilitate immobilization of the reagent or analyte to the solid support. In some embodiments, the reagent is provided pre-coupled to the solid support.

The kits can contain materials sufficient for one assay, or can contain sufficient materials for multiple assays.

Also featured in accordance with the present invention are methods for detecting glycosylated proteins in a sample. Such methods comprising contacting the sample with a lectin to form a complex between glycosylated proteins in the sample and the lectin, and then detecting the glycosylated protein-lectin complex. In some embodiments, the methods comprise contacting the sample with an antibody to capture glycosylated proteins in the sample. The antibody can be specific for a particular protein, for a particular glycosyl moiety, or for a particular protein-glycosyl moiety complex. The antibody can be coupled to a solid support. The sample can then be washed, and the lectin applied to the washed sample. The lectin can be coupled to a detectable moiety, and directly detected, or the lectin can be contacted with a secondary reagent coupled to a detectable moiety, e.g., an anti-lectin antibody, and then detected.

As will be appreciated, aspects of the present invention find great utility in the evaluation of the presence or absence of liver pathologies in humans. It will also be seen by persons of ordinary skill in the art that the present invention may be applied to animals, both for prognostic or diagnostic purposes, for the monitoring of therapeutic efficacy or otherwise in manners analogous to those methods useful in humans. Additionally, however, aspects of the present invention may be used to monitor the progress of animal studies in a research environment. Thus, assessment of glycosylation in circulating or other proteins in mice, rats, dogs and other animals can inform persons performing research involving such animals of the pathological status of the livers of such animals. In this way, for example, toxicity of proposed or existing pharmaceuticals, additives, adjuvants, industrial or agricultural chemicals or any of a wide variety of chemicals, biochemical species, environmental or industrial pollutants or other materials may be evaluated.

It will be seen that such evaluation of toxicity is useful in, e.g., drug trials preparatory to regulatory submissions. Additionally, the toxicity of a host of species may be evaluated in a direct, convenient way. Moreover, it is well known that many extant pharmaceuticals, including statins, antineoplastic agents and others have significant liver toxicity. Toxicity is also a concern when drugs are abused or overdosed. The present invention allows monitoring of such toxicity in these circumstances for pre- or post approval pharmaceutical or, indeed, for unlawful drugs.

The following examples are provided to describe the invention in more detail. They are intended to illustrate, not to limit the invention.

Example 1

General Experimental Procedures

Glycan Analysis. Serum was obtained from patients clinically diagnosed as infected with chronic HBV, and from patients clinically diagnosed as having HCC, patients clinically diagnosed as having liver cirrhosis, and from control subjects with no evidence of any liver disease. Serum samples were stored at −80° C. until analysis.

Protein aliquots (1 mg/mL) were denatured with 1% SDS, 50 mM β-mercaptoethanol for 10 min at 100° C. The solution was cooled, and supplemented with NP-40 to a concentration of 5.75%. PNGase F (ProZyme, San Leandro, Calif.) was added to a final concentration of 1 mU (IUB)/μL, and a cocktail of protease inhibitors was added to the mix. The solution was then incubated for 24 hours at 37° C. The oligosaccharides separated from the proteins in the sample were recovered and purified by solid phase extraction using a porous graphite matrix (LudgerClean H, Ludger Limited, Oxford, UK). Free oligosaccharides were labeled with 2-aminobenzamide, and purified using commercially available kits (Ludger Limited UK).

Fluorescently-labeled glycans were subsequently analyzed by HPLC using a normal phase column (TSK amide 80 column). The mobile phase consisted of Solvent A (50 mM ammonium formate, pH4.4) and Solvent B (acetonitrile) and the gradient used was as follows: linear gradient from 20-58% Solvent A at 0.4 mL/minute for 152 min, followed by a linear gradient from 58-100% Solvent A for the next 3 min. The flow rate was increased to 1.0 mL/minute and the column washed in 100% Solvent A for 5 min. Following the wash step, the column was equilibrated in 20% Solvent A for 22 min in preparation for the next sample run. HPLC analysis was performed using the Waters Alliance HPLC System, complemented with a Waters fluorescence detector, and quantified using the Millennium Chromatography Manager (Waters Corporation, Milford, Mass.). Glycan structures were identified by comparison to known standards and by sequential exoglycosidase digestion.

Lectin Extraction and Analysis.

Immunoglobulins were removed from the samples (media and serum) using a Protein A/G column (Pierce, Rockford, Ill.) prior to the lectin extraction. Samples were supplemented with a lectin binding solution, bringing the final concentration of the sample to 20 mM Tris buffered saline (TBS), 1 mM calcium chloride, 1 mM magnesium chloride, and 1 mM manganese chloride (pH 7.0). The samples were incubated for 16 hours at 4° C. with an array of agarose-bound fucose-recognizing lectins. These lectins consisted of Lens culinaris (LCH), Pisumsativum sativum (PSA) and Vicia faba (VFA) and recognize branched mannoses with the alpha fucose determinant (all purchased from EY laboratories, San Mateo, Calif.). Incubation was performed in a microcentrifuge tube prior to transfer to a Costar 0.45 μM Spin-X column (Corning, Acton, Mass.). The lectin column was washed thoroughly with lectin binding solution before the bound fraction was eluted using the appropriate inhibitory monosaccharides (200 mM methyl-α-D-glucopyranoside, 200 mM α-methyl-D-manno-pyranoside). The bound and unbound fractions were buffer exchanged into TBS using Milllipore YM-3 Centricon devices and subjected to glycan analysis or 2DE. Protein levels were monitored throughout all extractions.

2-Dimensional Gel Electrophoresis.

Samples were diluted in buffer (7M urea, 2M thiourea, 4% CHAPS, 65 mM DTT, 5 mM TBP, and 0.4% ampholytes), vortexed periodically for 1 h, and applied to an 18 cm pH3-10NL IPG strip (Amersham, Piscataway, N.J.). Gel rehydration was carried out for 14 h at 50 V, and focused using the Protean (Bio-RadLaboratories Headquarters, Hercules, Calif.) IEF apparatus. After focusing, gel strips were reduced in 6 M urea, 2% SDS, 1.5% DTT, 30% glycerol, and 50 mM Tris pH 6.8 for 10 min and alkalated in 6 M urea, 2% SDS, 3% iodoacetamide, 30% glycerol and 50 mM Tris pH 6.8. The second dimension was resolved with an 8-18% acrylamide-0.8% PDA gradient gel on a Protean II xi cell (Bio-Rad) with the running conditions set to 20 mA/gel for 20 min and 40 mA/gel for 4 h with gels cooled to 14° C. Gels were fixed (30% EtOH/5% phosphoric acid) and stained with a colloidal Coomassie brilliant blue stain. For all samples, gels were run in quadruplicate and only differences that were consistent in all gels were considered meaningful.

Gel Imaging and Analysis.

Gels were digitally imaged using a 16-bit cooled CCD camera (Fluor Chem 8000, Alpha Innotech, San Leandro, Calif.). TIFF files of the gel images were analyzed using NonLinear Dynamics Progenesis Workstation gel imaging software package (Nonlinear USA Inc., Durham, N.C.). The polypeptide features in each gel image were delineated and then the software determined the total intensity of pixels within each feature (the integrated intensity). Polypeptide features were normalized by using the integrated intensity of each feature and expressing it as a percent of the sum of integrated intensities of the entire gel.

Mass Spectrometry.

MALDI Analysis. Protein spots were excised from colloidal Coomassie blue stained gels, de-stained, and digested with trypsin. Recovered peptides were concentrated and desalted using Zip Tip C18 (Millipore, Bedford, Mass.) according to manufacturer's directions and prepared for MALDI-TOF mass spectrometry by mixing 0.5 μL of peptide mixture with 0.5 μL of 10 mg/mL of alpha-cyano 4-hydroxy cinnamic acid, 1% formic acid in 50% acetonitrile and allowing the droplet to dry on the MALDI plate. Peptide mass maps were obtained using a Voyager-DE ProMass Spectrometer (PE Biosystems, Foster City, Calif.) operated in positive ion reflectron mode. Proteins were identified from the peptide mass maps using the MASCOT online database www.matrixscience.com to search the nonredundant protein database.

LC MS/MS Analysis.

Peptide identification was performed on a ThermoFinnigan LCQ ion trap mass spectrometer (ThermoElectron Corporation, CA) equipped with on-line microcapillary HPLC (Eldex, Napa, Calif.) and microspray ionization source that was built in-house. The microspray consists of a microcapillary column, picotip 360×75 μm, with an integrated 15 μm tip (New objective, Woburn Mass.) self-packed with Reliasil C18 resin (Column Engineering, Ontario, Calif.) to a length of 10 cm. An aliquot of the sample was loaded via a pressure bomb into a capillary sample trap (Upchurch, Wash.) self-packed with C18, then placed just upstream of the microcapillary column. The HPLC is programmed to produce a 3 h gradient (5%-65% B) at 30 μL/min. Prior to the trap, passive flow splitting is used to reduce the flow down to ~500 nl/minute. Buffer A consists of 5% acetonitrile+1% acetic acid; buffer B consists of 90% acetonitrile+1% acetic acid. The LCQ was programmed to perform a full scan from 450 to 2000 m/z, followed by 3 data dependent MS/MS scans set to pick the most abundant ion species from the full scan.

Data Analysis and Interpretation.

Mass spectrometry data (spectra) was searched against the nonredundant human database using SeQuest (Thermo Electron Corporation). Peptides that score above the threshold value of 1.5×Corr (singly)/2.0×Corr (doubly)/2.5×Corr (triply) were then manually verified. In all cases, the bound peptides should contain the N-linked glycosylation sequon, N-X-S/T that has been converted to a D-X-S/T by the action of the PNGase F enzyme. This results in a Mass difference of 0.9840 Da as compared to the glycosylated sequence.

Immunoblotting.

Equal volumes of patient sera from either total serum (0.5 μL/lane), non lectin bound (unbound) or lectin bound (bound) were resolved by SDS-PAGE on 4-20% polyacrylamide gradient gels. The proteins were transferred to a PVDF membrane by immunoblotting. The membranes were blocked by incubating with a blocking buffer of 1×TBS (50 nM Tris-HCl, pH 7.6, 150 mM sodium chloride) made 5% nonfat dried milk, and 0.1% Tween 20 for 1 h at room temperature. The blots were then incubated overnight with desired antibody and developed using chemiluminescent detection system ("ECL Plus," Amersham Pharmacia Biotech, Arlington Heights, Ill.). Blots were visualized using an AlphaInnotech Fluor Chem CCD camera with AlphaEase spot densitometry software (AlphaInnotech Corp., San Leandro, Calif.).

Example 2

Core Fucosylation is Increased in Hepatocellular Carcinoma

Figure 1:
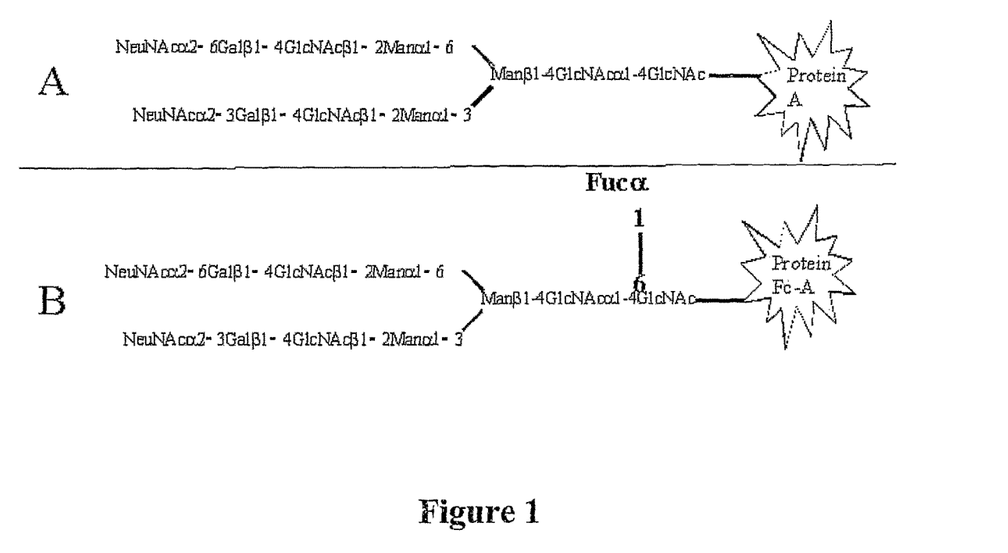
Figure 2A:
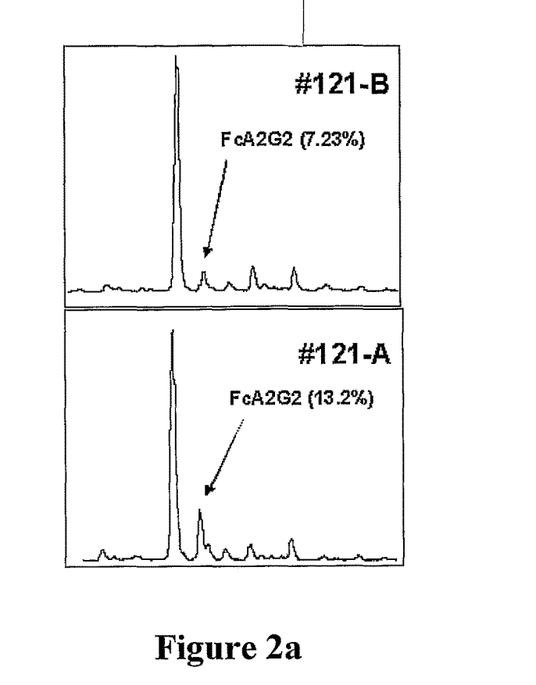
Figure 2B:
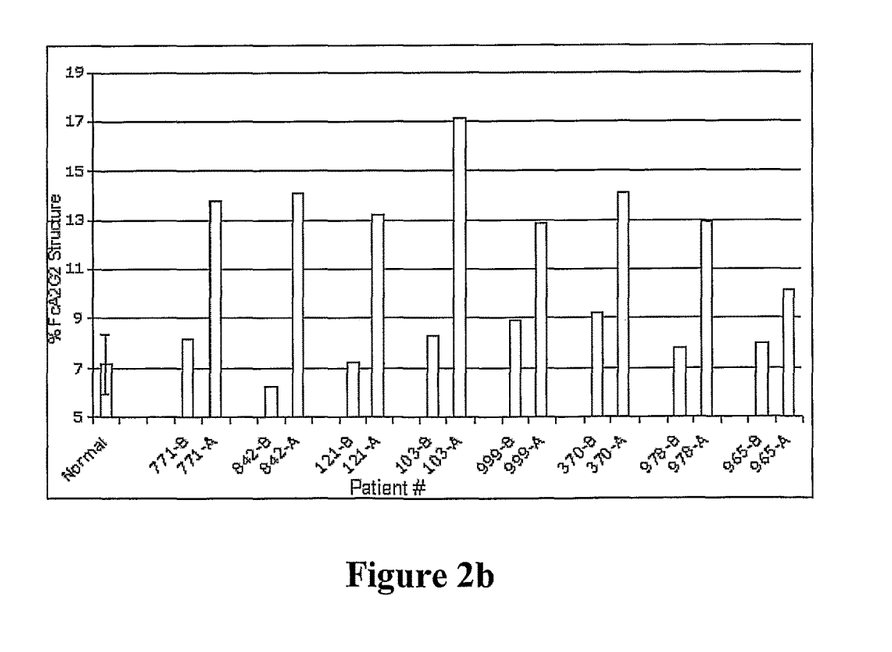

A targeted glycoproteomic methodology that allows for the identification of glycoprotein biomarkers in serum was developed. The methodology first identifies changes in N-linked glycosylation that occur with the disease. These changes act as a tag so that specific proteins that contain that glycan structure can be extracted. Initial experiments in an animal model revealed a protein, GP73, that is more sensitive at detecting HCC than currently used markers such as AFP. In the animal model of HCC, the change in glycosylation was an increase in core fucosylation (Block et al. 2005). This change was also observed in people who developed HCC. An example of the increase in fucosylation is shown in FIG. 2. This sample set consisted of 16 samples from 8 patients at two time points: before the development of cancer, and after the diagnosis of cancer. In this case, all patients classified as before were clinically diagnosed with cirrhosis. Samples classified as after were clinically diagnosed with HCC by ultrasound and biopsy. As this figure shows, patients before the diagnosis of HCC have much lower levels of the core fucosylated bi-antennary glycan (FcA2G2) as compared to after the diagnosis of HCC. For example, patient 121 had 7.23% of the FcA2G2 glycan before the diagnosis of HCC and 13.2% after the diagnosis of HCC. As seen in FIG. 2B, this upward trend was true of all patients examined. These results highlight the fact that increased levels of α-1,6 linked core fucosylation are associated with the development of HCC. This is true in samples that were AFP positive (>20 ng/ML) or AFP negative. That is, as shown in FIG. 2B, patients 965, 370, 842, 999 and 978 were all AFP negative, yet had increased levels of the FcA2G2 glycan. For all the patients examined so far those who are normal, have active hepatitis, or have cirrhosis had an average of 8.44%+/−0.75 (n=19) of the core fucosylated glycan, while those patients diagnosed with HCC had an average of 12.5%+/−1.83 (n=17) of the core fucosylated glycan. This difference was statistically different with a P value of 0.001.

Example 3

Identification of Fucosylated Glycoproteins in Hepatocellular Carcinoma

Figure 4:
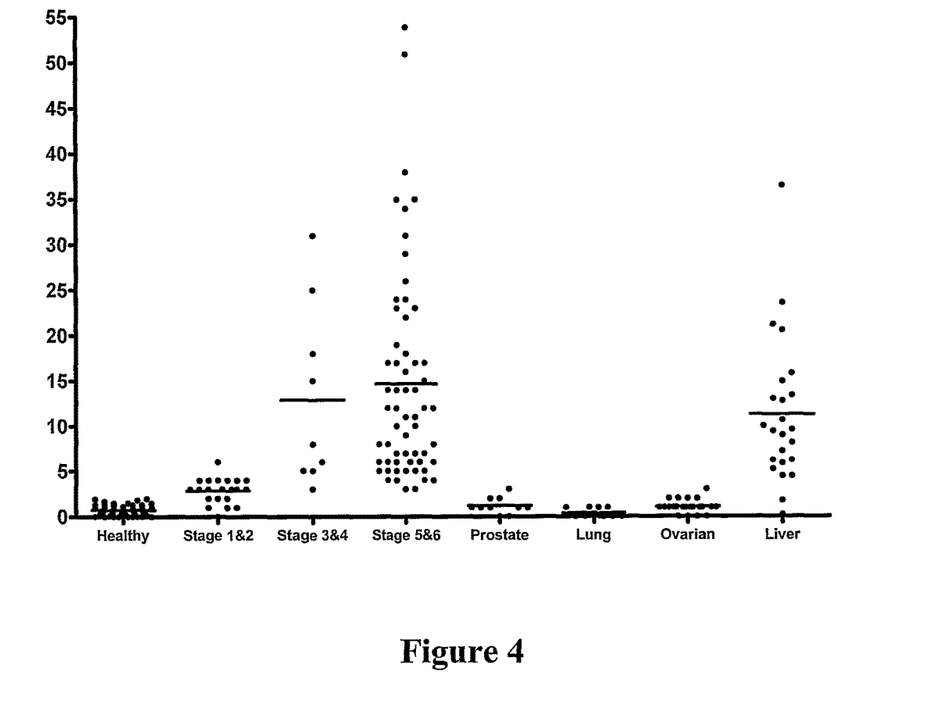
FIG. 4 shows a lectin analysis of human immunoglobulins in patients with varying degrees of liver disease. Lectin ELISAs were performed as described in FIG. 3 and the examples, except the lectin AAL (*Aleuria aurantia* lectin) was used. 5 μl of human serum was used in the assay. This figure shows an increase in the level of fucosylated immunoglobulin with increasing fibrosis. The differences between the cirrhotic group and the healthy, stage 1&2 groups is statistically significant with a $p<0.001$ as determined by Student's t-test.

As the level of fucosylation was increased in patients with HCC, it was imperative to determine those proteins that had increased fucosylation. Therefore, the fucosylated glycoproteins associated with sera from either pooled normal or pooled HCC positive individuals were extracted using lectins and the proteome analyzed by either two dimensional gel electrophoresis (2DE) or by a simple LC MS/MS based methodology. Using these methodologies it was observed that glycoproteins such as fucosylated (Fc) α-1-acid glycoprotein, Fc-ceruloplasmin, Fc-α-2-macroglobulin, Fc-hemopexin, Fc-Apo-D, Fc-HBsAg, and Fc-Kininogen increased in patients with HCC, while the levels of Fc-haptoglobin decrease in the those patients (Table 1). Interestingly, several immunoglobulin molecules (IgG, IgA and IgM) were also found in the fucosylated proteome of those patients with cancer. However, further analysis has shown that these proteins become fucosylated primarily in cirrhosis and not just cancer (FIG. 4).

TABLE 1

Proteins identified as altered in patients with HCC.

Fc-GP-73
Fc-Hemopexin
Fc-HBsAg
Fc-hepatitis B viral particle
Fc-alpha-acid-glycoprotein
Fc-alpha-1-antichymotrypsin (including
Fc-Alpha-1-antichymotrypsin His-Pro-less)
Fc-alpha-1-antitrypsin
Fc-Serotransferrin
Fc-Ceruloplasmin
Fc-alpha-2-macroglobulin
Fc-alpha-2-HS-glycoprotein (Fetuin A)
Fc-Haptoglobin
Fc-Fibrinogen gamma chain precursor
Fc-IgG
Fc-IgA
Fc-APO-D
Fc-IgM
Fc-Kininogen
Fc-Histidine rich glycoprotein
Fc-Complement factor 1 precursor (including Fc-Complement factor I heavy chain
Fc-Complement factor I light chain)
Fc-Complement C1s component
Fc-Complement factor B precursor (including Complement factor B Ba fragment and Fc-Complement factor B Bb fragment)
Fc-Complement C3 precursor (including Fc-Complement C3 beta chain
Fc-Complement C3 alpha chain
Fc-C3a anaphylatoxin
Fc-Complement
C3b alpha' chain
Fc-Complement C3c fragment

TABLE 1-continued

Proteins identified as altered in patients with HCC.

Fc-Complement C3dg fragment
Fc-Complement C3g fragment
Fc-Complement C3d fragment and Fc-Complement C3f fragment)
Fc-Complement C5 (including Fc-Complement C5 beta chain
Fc-Complement C5 alpha chain
Fc-C5a anaphylatoxin
Fc-Complement C5 alpha' chain)
Fc-Complement C7
Fc-alpha-1 B glycoprotein
Fc-B-2-glycoprotein (apo H)
Fc-Vitamin D-binding protein
Fc-Inter-alpha-trypsin inhibitor heavy chain H2
Alpha-1B-glycoprotein
Fc-Angiotensinogen precursor
Fc-Angiotensin-1
Fc-Angiotensin-2
Fc-Angiotensin-3
Fc-GARP protein
Fc-beta-2-glycoprotein
Fc-Clusterin (Apo J)
Integrin alpha-8 precursor glycoprotein (including
Fc-Integrin alpha-8 heavy chain and Fc-Integrin alpha-8 light chain
Fc-hepatitis C viral particle
Fc-Leucine-rich repeat-containing protein 32 precursor.

Example 4

Levels of Fc-GP73 and Fc-Hemopexin are Increased in Patients with Hepatitis B-Induced Hepatocellular Carcinoma The level of Fc-GP73 and Fc-hemopexin were examined in a small blinded patient cohort (from our collaborator Dr. Chau-Ting Yeh, Director, Digestive core lab and Hepatoma research team, Liver Research Unit, Chang Gung Memorial Hosp, Taiwan) containing a total of 80 patients with varying degrees of liver disease (Table 2). Analysis of these samples was performed for total GP73 level, for the level of fucosylated GP-73 (Fc-GP73), and for the level of fucosylated hemopexin (Fc-hemopexin). Total GP73 was analyzed by immunoblot using whole serum. Fucosylated species were analyzed by lectin extraction of 5 µl of serum (LCH) followed by immunoblotting of the fucosylated fraction and imaging using an AlphaInnotech Fluor Chem CCD camera with AlphaEase spot densitometry software. The sensitivity, specificity, and positive predicative values for these three markers are presented in Table 3. As this figure shows, using a cut-off of 5 fold greater then purchased healthy serum (Sigma Chemical Co., St. Louis, Mo.) total GP73 had a sensitivity of 65% and a specificity of 90%, which was very similar to our larger blinded study using this marker (Marrero et al. (2005) J. Hepatol. 43:1007-12); 69% sensitivity and 86% specificity). Even more promising then total GP73 were Fc-GP73 and Fc-hemopexin. Fc-GP73 had a sensitivity of 90% and a specificity of 100% (using a cut-off of 100 fold greater then purchased healthy serum (Sigma Chemical Co), while Fc-hemopexin had a sensitivity of 95% and a specificity of 100% (using a cut-off of 20 fold greater then purchased healthy serum (Sigma Chemical Co.).

TABLE 2

Samples utilized to compare the predictive value of markers in HBV induced liver disease.

| Group | Clinical Status* | Number | Age Range |
|---|---|---|---|
| 1 | Healthy Subjects | 20 | 21-64 |
| 2 | HBV+, inactive (carrier) | 20 | 26-70 |
| 3 | HBV+, active (Cirrhosis) | 20 | 22-68 |
| 4 | HBV infected, HCC | 20 | 25-81 |
| Sigma Serum | Commercially available serum | 1 | unknown |

*clinical status was determined by lack of HBsAg (group 1), presence of HBsAg (group 2), presence of HBsAg along with biopsy to confirm cirrhosis (group 3), or presence of HBsAg along with the diagnosis of HCC by MRI (group 4)

TABLE 3

Sensitivity, specificity, and positive predictive value of total GP73, Fc-GP73, and Fc-hemopexin in the patients shown in Table 2.

| Marker | Sensitivity | Specificity | PPV |
|---|---|---|---|
| Total GP73 | 65% | 90% | 77% |
| Fc-GP73* | 90% | 100% | 100% |
| Fc-Hemopexin* | 95% | 100% | 100% |

*Analysis of Fc-GP73 and Fc-hemopexin was performed via immunoblot following Ig-depletion and lectin extraction.

Example 5

Lectin ELISA for Fc-AFP and Fc-Kininogen

Figure 3:
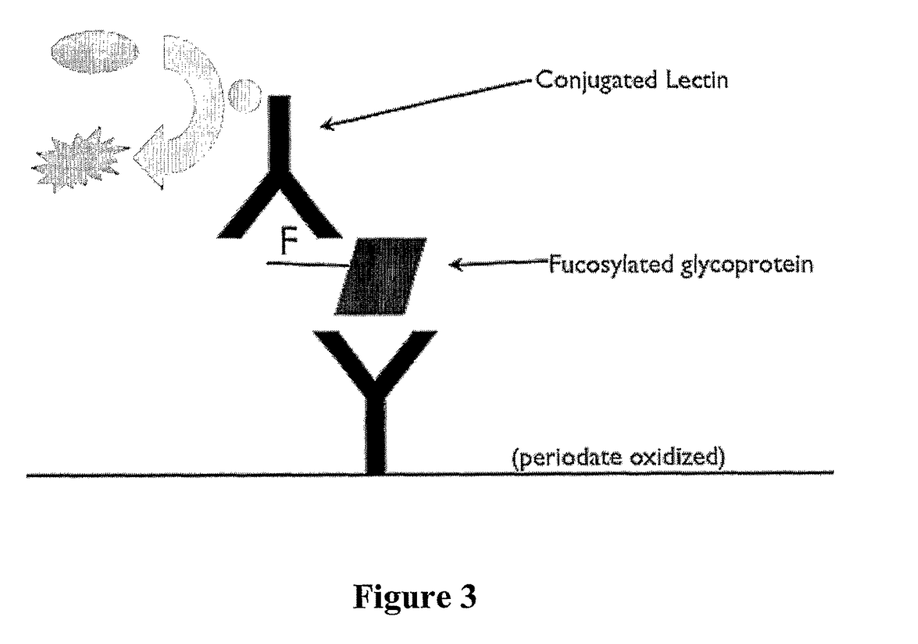

The analysis of fucosylated GP73 and fucosylated hemopexin in Table 3 was performed by immunoblot of the fucosylated proteome. This required the removal of immunoglobulin and lectin extraction of each sample. As this is quite laborious, a lectin-ELISA to allow for much higher throughput was developed (see FIG. 3). Initial experiments focused on the development of a lectin-ELISA for Fc-AFP. AFP is known to be fucosylated and several reports in the literature were available to allow for comparison (Naitoh et al (1999) J. Gastroenterol. Hepatol. 14:436-45). For assay development, a selected sample set of 60 patients was utilized as previously described (Marrero et al. (2005) J. Hepatol. 43:1007-12). 20 patients were infected with HCV but otherwise considered healthy, 20 patients were infected with HCV and diagnosed with cirrhosis, and 20 patients were infected with HCV and diagnosed with HCC. The samples in this set were chosen to include many AFP+ individuals. In addition, human serum (Sigma Chemical Co.) was utilized as a control to which all other patients groups were compared. Briefly, 50 µl of human serum is diluted in 150 µl of lectin-binding buffer (20 mM Tris, 1 mM CaCl2, 1 mM MgCl2, and 1 mM MoCl2 chloride, pH 7.0) and added directly to the Heterophilic Blocking Tubes prior to addition to plates for 2 hours at 370 C. Subsequently, plates were washed 10 times with 2% Tween 20 in lectin binding buffer before lectin was added. Fucosylated glycoforms were detected, with a biotin labeled *Lens Culinaris* or *Aleuria aurantia* lectin (Vector Laboratories, Burlingame, Calif.). Lectin was detected using a fluorescein labeled streptavidin system and subsequently, samples were measured in the Cytofluor 4000 Fluorescence Plate Reader (MTX Lab Systems, Inc. Vienna, Va.) at the appropriate wavelength. The relative fluorescent intensity in each sample was compared to that observed in purchased normal serum. Table 4 shows the results of the analysis with Fc-AFP. In this sample set, using a cut-off of 5 fold greater then purchased healthy serum (Sigma Chemical Co.), Fc-AFP had a sensitivity of 70%, a specificity of 90% and a positive predicative value (PPV) of 91%. This is consistent with what has been reported with Fc-AFP (Naitoh et al.

(1999) J. Gastroenterol. Hepatol. 14:436-45). In this same sample set, total AFP had a sensitivity of 70%, a specificity of 70%, and a PPV of 77% (using a cut-off of 20 ng/ml). Using the same sample set, Fc-kininogen was analyzed using the same methodology as for AFP. Fc-Kininogen was identified in proteomic analysis as being present in the cancer samples and utilized initially as the antibody was easily available. As Table 4 shows, Fc-kininogen had a sensitivity of 80%, a specificity of 95% and a PPV of 95% (using a cut-off of 3 fold greater then purchased healthy serum (Sigma Chemical Co).

TABLE 4

Sensitivity, specificity, and PPV for total AFP, fucosylated AFP, and fucosylated kininogen as determined by Lectin-ELISA.

| Marker | Sensitivity | Specificity | PPV |
| --- | --- | --- | --- |
| AFP | 70% | 70% | 77% |
| Fc-AFP | 70% | 90% | 91% |
| Fc-Kininogen | 80% | 95% | 95% |

Example 6

Human Immunoglobulins Become Fucosylated with the Development of Cirrhosis

As shown in Table 1, over 50 glycoproteins that have altered glycosylation as a function of liver disease have been identified. Although the increase in many of these fucosylated glycoproteins correlates with the development of hepatocellular carcinoma (HCC), some of these glycoproteins were found to alter with other liver diseases as well. For example, it was observed that human Immunoglobulins become hyper-fucosylated with the development of liver cirrhosis. Since IgG was determined to be the major source of fucosylated protein in the serum of those with cirrhosis, in the initial small set of samples, it was reasoned that the level of fucosylated IgG might correlate with a diagnosis of cirrhosis. Moreover, based on the results shown in FIG. 3 and Table 4, it seemed that a simple lectin based assay could be developed to detect fucosylated IgG.

Briefly, fucosylated IgG was detected by incubating 5 µl of serum with wells coated with periodate oxidized mouse anti-human IgG for 2 hours. Subsequently fucosylated human IgG was detected by incubation with biotinylated *Aleuria aurantia* lectin (AAL). Bound lectin was detected using RDye™ 800 Conjugated STREPTAVIDIN and signal intensity measured using the Odyssey® Infrared Imaging System (LI-COR Biotechnology, Lincoln, Nebr.). In all cases sample intensity was compared to commercially purchased human serum (Sigma Chemical Co.).

Using this assay, the relative amount of fucosylated IgG was determined in more than 200 serum samples from with normal patients, or those with varying degrees of liver disease. In addition, patients with non-liver diseases were examined. It is important to note that the operator of the fucosylated IgG detection assay was not aware of the diagnosis associated with serum sample, at the time of the testing. The results are shown in FIG. 4.

The results are expressed as fold increase over sigma. The signal detected in the samples from the 70 healthy subjects (no evidence of HBV, HCV or liver disease) was consistently low, less than 2 fold of that observed in commercially purchased serum. In contrast, all of the cirrhosis patients had values greater than 2 fold above commercially purchased serum. The mean level of increase was 13-fold above commercially purchased serum. HCV infected patients with varying levels of fibrosis also had elevated levels of fucosylated IgG. Interestingly, the level of fucosylated IgG varied in these patients based upon the level of fibrosis. Those patients with stage 0-2 fibrosis had a mean 3 fold increase in fucosylated IgG while those patients with stage 4 or greater fibrosis had a mean 13 fold increase in fucosylated IgG. Using a cut-off of 5 fold above commercially purchased human serum, this assay had a sensitivity of 92%, a specificity of 96% at differentiating stage 1-2 fibrosis from stage 3-6 fibrosis/cirrhosis. The positive predictive value was 92% and the negative predictive value was 96%.

The present invention is not limited to the embodiments described and exemplified above, but is capable of variation and modification within the scope of the appended claims.

What is claimed:

1. A kit for assessing the pathological status of a liver in a subject suspected of having a liver pathology comprising:
    a deglycosylated capture reagent for isolating from a biological fluid a protein selected from GP73, HBsAg, hepatitis B viral particle, alpha-1-antichymotrypsin, alpha-1-antichymotrypsin His-Pro-less, Ceruloplasmin, alpha-2-macroglobulin, Haptoglobin, Fibrinogen gamma chain precursor, APO-D, Kininogen, Histidine rich glycoprotein, Complement factor 1 precursor, complement factor I heavy chain, complement factor I light chain, Complement C1s, Complement factor B precursor, complement factor B Ba fragment, Complement factor B Bb fragment, Complement C3 precursor, Complement C3 beta chain, Complement C3 alpha chain, C3a anaphylatoxin, Complement, C3b alpha' chain, Complement C3c fragment, Complement C3dg fragment, Complement C3g fragment, Complement C3d fragment, Complement C3f fragment, Complement C5, Complement C5 beta chain, Complement C5 alpha chain, C5a anaphylatoxin, Complement C5 alpha' chain, Complement C7, alpha-1 B glycoprotein, Vitamin D-binding protein, Inter-alpha-trypsin inhibitor heavy chain H2, Alpha-1B-glycoprotein, Angiotensinogen precursor, Angiotensin-1, Angiotensin-2, Angiotensin-3, GARP protein, beta-2-glycoprotein, Clusterin (Apo J), Integrin alpha-8 precursor glycoprotein, Integrin alpha-8 heavy chain, Integrin alpha-8 light chain, hepatitis C viral particle, elf-5, HSP33-homolog, lysyl endopeptidase or Leucine-rich repeat-containing protein 32 precursor, wherein said capture reagent for isolating said protein is specific to said protein;
    a reagent that binds to core fucosyl moieties on said isolated protein, wherein the binding of said reagent is determinative as to the presence of a core fucosyl moiety on said protein;
    a detection reagent for detecting the reagent bound to the fucosyl moieties to provide a detected core fucosylation value, and instructions for using the kit in a method for assessing the pathological status of the liver by comparing the detected core fucosylation value with a reference value for core fucosylation on said protein in a comparable biological fluid of subjects without said liver pathology, said detected core fucosylation value relative to the reference value being indicative of the presence or absence of said liver pathology, wherein a detected core fucosylation value that deviates from said reference value to a statistically significant degree is indicative of the presence of said liver pathology, or comparing the detected core fucosylation value with a reference value for core fucosylation on said protein in a comparable biological fluid of subjects in which said liver pathology is known to be present, said detected core fucosylation value relative to the reference value being indicative of the presence or absence of said liver pathology, wherein a detected core fucosylation value that deviates from said reference value to a statistically significant degree is indicative of the absence of said liver pathology.

2. The kit of claim 1, wherein said reagent that binds to fucosyl moieties comprises a molecule that directly labels an oligosaccharide.

3. The kit of claim 1, wherein said reagent that binds to fucosyl moieties comprises a molecule that is coupled to a detectable moiety.

4. The kit of claim 1 further comprising a secondary reagent that specifically recognizes said reagent that binds to fucosyl moieties, wherein said secondary reagent is coupled to a detectable moiety.

5. The kit of claim 1 wherein said reagent that binds to fucosyl moieties comprises a lectin.

6. The kit of claim 1 further comprising a solid support to which said capture reagent for isolating said protein is coupled.

7. The kit of claim 1 further comprising a positive control, a negative control, or both.

8. The kit of claim 1 wherein said reagents and said instructions are configured to permit multiple assessments using said kit.

9. The kit of claim 1 wherein said capture reagent for isolating said protein is an antibody.

10. The kit of claim 1, wherein the capture reagent for isolating said protein is specific to kininogen.

* * * * *

UNITED STATES PATENT AND TRADEMARK OFFICE
CERTIFICATE OF CORRECTION

PATENT NO. : 10,082,512 B2
APPLICATION NO. : 11/913348
DATED : September 25, 2018
INVENTOR(S) : Timothy M. Block et al.

Page 1 of 1

It is certified that error appears in the above-identified patent and that said Letters Patent is hereby corrected as shown below:

In the Specification

<u>Column 1,</u>
Lines 16-19, delete "This invention was made with government support under Grant Numbers R33CA94340 and U01 CA84951 awarded by NCI. The government has certain rights in the invention." and insert -- This invention was made with government support under Contract Nos. R33 CA094340 and CA084951 awarded by the National Institutes of Health. The government has certain rights in the invention. --.

Signed and Sealed this
Twentieth Day of November, 2018

Andrei Iancu
*Director of the United States Patent and Trademark Office*